United States Patent
Saltykov et al.

(10) Patent No.: US 9,474,473 B2
(45) Date of Patent: Oct. 25, 2016

(54) METHOD TO MEASURE REAL-EAR-TO-COUPLER DIFFERENCE

(75) Inventors: Oleg Saltykov, Fairlawn, NJ (US); Anton Gebert, Kleinsendelbach (DE)

(73) Assignee: Sivantos Pte. Ltd., Singapore (SG)

( * ) Notice: Subject to any disclaimer, the term of this patent is extended or adjusted under 35 U.S.C. 154(b) by 216 days.

(21) Appl. No.: 14/350,402

(22) PCT Filed: Nov. 8, 2011

(86) PCT No.: PCT/US2011/059732
§ 371 (c)(1),
(2), (4) Date: Apr. 8, 2014

(87) PCT Pub. No.: WO2013/070192
PCT Pub. Date: May 16, 2013

(65) Prior Publication Data
US 2014/0296739 A1 Oct. 2, 2014

(51) Int. Cl.
*A61B 5/00* (2006.01)
*A61B 5/12* (2006.01)
*H04R 25/00* (2006.01)

(52) U.S. Cl.
CPC .............. *A61B 5/126* (2013.01); *A61B 5/125* (2013.01); *A61B 5/6817* (2013.01); *A61B 5/7235* (2013.01); *H04R 25/70* (2013.01); *H04R 2460/05* (2013.01)

(58) Field of Classification Search
CPC ........ A61B 5/12; A61B 5/121; A61B 5/123; A61B 5/125; A61B 5/126; H04R 25/00; H04R 25/02; H04R 25/70; H04R 29/00
See application file for complete search history.

(56) References Cited

U.S. PATENT DOCUMENTS

| | | |
|---|---|---|
| 6,154,546 A | 11/2000 | Uvacek |
| 6,658,122 B1 | 12/2003 | Westermann et al. |
| 8,045,737 B2 | 10/2011 | Stirnemann |
| 2008/0260192 A1 | 10/2008 | Yanz et al. |
| 2010/0202642 A1 | 8/2010 | LoPresti et al. |
| 2010/0260343 A1 | 10/2010 | Recker et al. |

OTHER PUBLICATIONS

Chan J C K et al, "Estimation of Eardrum Acoustic Pressure and of Ear Canal Length From Remote Points in the Canal", The Journal of the Acoustical Society of America, American Institute of Physics for the Acoustical Society of America, New York, NY, US, vol. 87, No. 3, (Mar. 1, 1990), XP009035813,ISSN 0001-4966, p. 1237-1247.
Kevin J. Munro et al, "Measuring the Real-Ear to Coupler Difference Transfer Function With an Insert Earphone and a Hearing Instrument: Are They the Same?", Ear and Hearing, vol. 26, No. 1, (Feb. 1, 2005) pp. 27-34, XP055011871.
International Search Report dated Mar. 5, 2012 in Internal Application No. PCT/US11/59732, 9 pages.

*Primary Examiner* — Max Hindenburg
(74) *Attorney, Agent, or Firm* — Laurence A. Greenberg; Werner H. Stemer; Ralph E. Locher

(57) ABSTRACT

A method (10) of obtaining acoustical measurements of an individual ear that are compensated for errors caused by ear canal resonances.

14 Claims, 13 Drawing Sheets

METHOD TO MEASURE REAL-EAR-TO-COUPLER DIFFERENCE

FIELD OF INVENTION

The present invention generally relates to the acoustical measurement of an individual ear. More particularly, the present invention relates to acoustical measurements of an individual ear that are compensated for ear canal resonances.

BACKGROUND OF THE INVENTION

The Real-Ear-To-Coupler Difference (RECD) is a unique acoustical measure for an individual ear that allows for prediction of sound pressure level (SPL) at the eardrum by using the results of SPL measured in a 2-cc coupler. Briefly, in order to quantify measurements related to the ear, it is common practice to simulate an average ear using certain mechanical and acoustical systems. An ear simulator (like a coupler) is an example of such a simulation system, having the same acoustic input impedance as an average occluded ear.

The main purpose of RECD is to simplify the procedure of evaluation of the ear canal SPL of an individual. The measure of difference in SPL directly reflects the difference in impedances between the individual ear and the 2-cc coupler. If the sound pressure of the occluded ear (e.g. an ear having a hearing aid inserted therein) was the same at the reference plane (R.P.) of the ear (e.g., at the ear tip) and at the eardrum, then a ratio of impedances of the occluded ear and the coupler could be used to define RECD. But it is well known that the sound pressure along the occluded ear canal will change rapidly at high frequencies because of forming standing waves. Therefore, one must distinguish between the input and the output of the occluded ear (i.e., the reference plane and the ear drum, respectively), which requires the use of the transfer impedance.

A description of obtaining an RECD with a high impedance sound source and an HA-1 coupler can be found in a review chapter of a book by Lawrence J. Revit, edited by Michael Valente, entitled "Strategies for Selecting and Verifying Hearing Aid Fittings", 2002, Chapter 3: Real-Ear Measures, second edition, Thieme Medical Publishers, Inc., New York and Stuttgart, 2002, which is incorporated by reference herein. The measurement procedure includes:

1. Attach the high-impedance sound source (such as, an insert earphone or a hearing aid) with the ear tip (usually surrounded with foam) to an HA-1 coupler. Measure and record the sound pressure registered by a probe microphone (2-cc SPL probe).
2. Detach the foam ear tip from the HA-1 coupler and insert it into the ear canal. Measure and record the SPL registered by the probe microphone (Ear canal SPL Probe).
3. Calculate RECD as eardrum response as RECD=(Ear canal SPL) minus (HA-1 SPL).

RECD measurement errors due will occur if the probe microphone is placed at a distance from the eardrum. The occluded ear canal can be presented as a tube with a length L that is individual for each person. Such a tube in combination with elements that simulate the impedance of the middle ear (eardrum, incus, cochlea, etc.) creates ear canal resonance and associated standing waves. Due to the standing waves, the sound pressure at the eardrum will be different from the sound pressure at a distance from the eardrum. FIG. 1 is a simplified mode of an ear canal and the sound pressure distribution in case of a ¼ wavelength standing wave.

The standing waves in the occluded ear canal will cause RECD measurement errors that depend on the depth of insertion of the probe microphone (further described in a technical application note by Per V. Bruel, et al., "Impedance of Real and Artificial Ears", 1976, Bruel & Kjaer Sound & Vibration Measurement A/S, Denmark). The shorter the distance from the eardrum to the probe microphone, the fewer amount of errors will occur. Simulated RECD errors for different positions of the probe microphone in the ear canal (11 mm for the length of the ear canal×7.5 mm for the diameter of the ear canal) are shown on FIG. 2. The occluded canal length is 11 mm (an average ear canal of an adult). The sound pressure SPL is normalized over the sound pressure SPL at the eardrum.

The Revit reference, cited above, recommends placing the probe microphone not farther than 6 mm from the eardrum so that the RECD errors due to the standing waves will not exceed 2 dB at 6 kHz (sound source frequency) and 4 dB at 8 kHz (sound source frequency). In practice, it is quite difficult to position the probe microphone deep into the ear canal so significant errors could occur if the probe microphone is placed incorrectly.

A recent U.S. Patent Publication (U.S. Patent Publication No. 2010/0202642 by Janice LoPresti and Tao Zhang, entitled "Method To Estimate The Sound Pressure Level At Eardrum Using Measurements Away From The Eardrum", filed Jan. 11, 2010) describes an alternative method of measuring SPL at the eardrum with the probe microphone (without using RECD). Specifically, the LoPresti reference suggests placing the probe microphone at a fixed distance from the sound source (5 mm). The expected shape of the SPL in the ear canal should have a notch at a frequency of a ¼ wavelength resonance of the ear canal. The LoPresti reference further proposes to locate the notch frequency F; calculate the quality factor Q of the notch; calculate the correction based on the Q and F values, and use the correction to compensate for the effect of the ear canal resonance. In practical use, the method proposed will not work, because the LoPresti reference addresses errors of SPL measured in the ear canal. The shape of the frequency responses of SPL in the ear canal will depend on many factors besides the ear canal resonances, so it could be very difficult, if not impossible, to identify the notch at an SPL response that is related to the ear canal resonance. FIG. 3 illustrates the problem of identifying the frequency F and the quality factor Q of the notch, caused by the ear canal resonance. The expected notch frequency F is between 6000 and 7000 Hz and can not be easily identified because the SPL responses depend on many factors other than the ear canal resonance.

SUMMARY OF THE INVENTION

The aforementioned problems are obviated by the present invention which provides a method of compensating for sound pressure measurement errors caused by ear canal resonance occurring in an occluded ear canal, comprising measuring the sound pressure of a sound source in an ear simulator; measuring the sound pressure of the sound source in the ear canal; calculating a real-ear-to-coupler difference (RECD) measurement using the sound pressure measurements; and calculating a corrected RECD measurement using a parameter of the RECD measurement. The calculating a corrected RECD measurement step may comprise calculating a correction to the RECD measurement to compensate for errors caused by ear canal resonance and combining the RECD measurement calculation and the correction calculation to obtain a corrected RECD measurement. The calculating a corrected RECD measurement step may also comprise measuring the frequency of the ear canal resonance and its specific frequencies at −3 dB from the level at the ear canal resonance. The parameter may comprise a notch frequency caused by ear canal resonance. The measuring the sound pressure of the sound source in the ear canal step may comprise measuring the sound pressure of the sound source in the ear canal near a reference plane of the ear.

Further, both sound pressure measurements may be made over the same frequency range of the sound generated by the sound source. The sound pressure may be registered by a sound pressure level (SPL) probe positioned near the sound source. In such case, the sound pressure measurements may be stored by a processor with a tangible data storage medium that may be operatively connected to the SPL probe. Also, the SPL probe may comprise a probe microphone. Also, the SPL probe may comprise a specially-adapted microphone of a hearing aid facing the ear canal.

Further, the ear simulator may comprise a 2 cc coupler or, alternatively, a specially-adapted coupler with an internal volume less than 2 cc. The sound source may comprise an insert earphone or a hearing aid.

The present invention also provides a method of measuring the sound pressure level (SPL) at an eardrum, comprising calculating real-ear-to-coupler difference (RECD) as the difference between an ear canal SPL and a simulated ear SPL; identifying a frequency notch in the RECD calculation associated with ear canal resonance; and obtaining and applying a correction to the RECD that compensates for ear canal resonance measurement errors. The obtaining and applying step may comprise calculating the correction as a frequency response of a complex transfer function over a selected frequency range. Parameters of the complex transfer function may comprise the identified frequency notch and the quality factor of the frequency notch. Alternatively, the obtaining and applying step may comprise calculating the correction using the following:

$$\mathrm{Corr} = 20 * \log \left| \frac{s*K}{(s*K)^2 + \frac{s*K}{Q} + 1} + 1 \right|,$$

where $s := i \cdot 2 \cdot \pi \cdot f$, a complex operator; $i := \sqrt{-1}$; f is the current frequency in Hz; Q is the quality factor of the notch; K is a frequency scaling factor equal to $\pi/(20*F)$; and F is the frequency of the notch in Hz.

The current frequency f may comprise a value in the range of 100 Hz-10 kHz.

The present invention also provides a method of measuring real-ear-to-coupler difference (RECD) for an ear under examination, comprising obtaining the difference of the results of two sound pressure level measurements made of the same sound source on two different loads in the ear over a frequency range of the sound source; characterizing an RECD curve from the obtained differences and a correction curve by the shape of the RECD curve near a frequency notch related to ear canal resonance; and obtaining a corrected RECD curve from the application of the correction curve to the RECD curve. Parameters of the correction curve may comprise the frequency notch and the quality factor of the frequency notch.

BRIEF DESCRIPTION OF THE DRAWINGS

For a better understanding of the present invention, reference is made to the following description of an exemplary embodiment thereof, and to the accompanying drawings, wherein.

DETAILED DESCRIPTION

Figure 1:
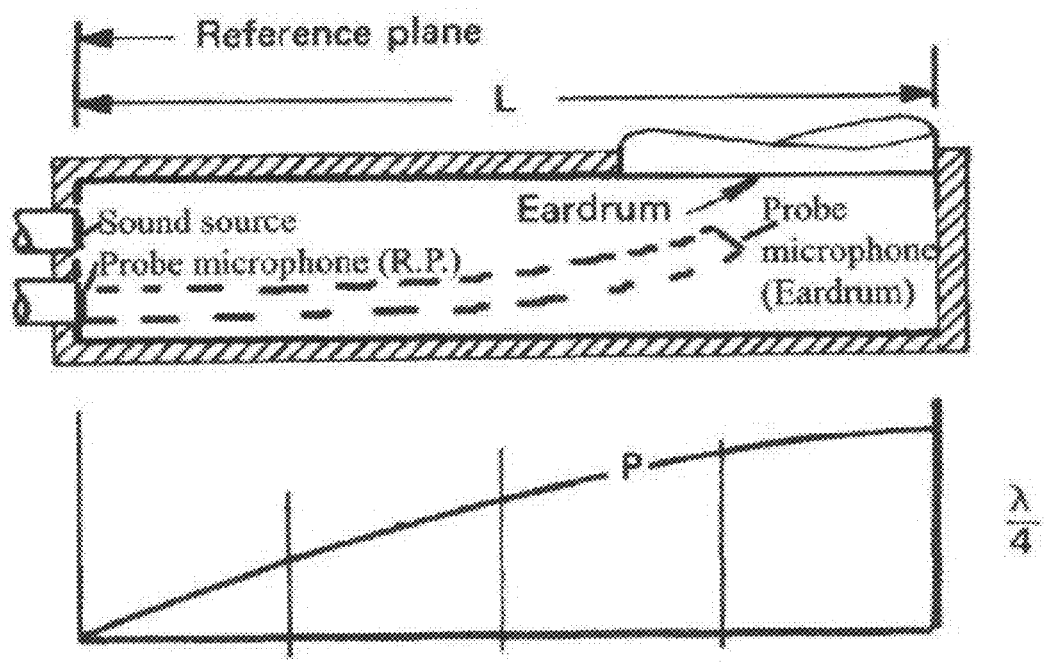
FIG. 1 is a simplified mode of an ear canal and the sound pressure distribution in case of a ¼ wavelength standing wave.
Figure 2:
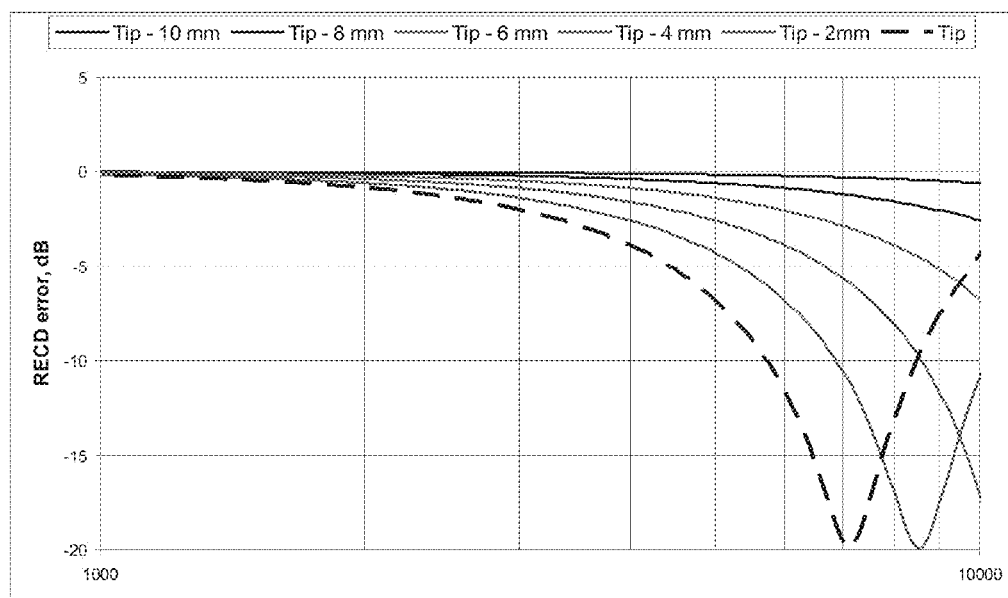
FIG. 2 is a graph of the errors of RECD caused by a probe microphone positioned at certain distances from the eardrum.
Figure 3:
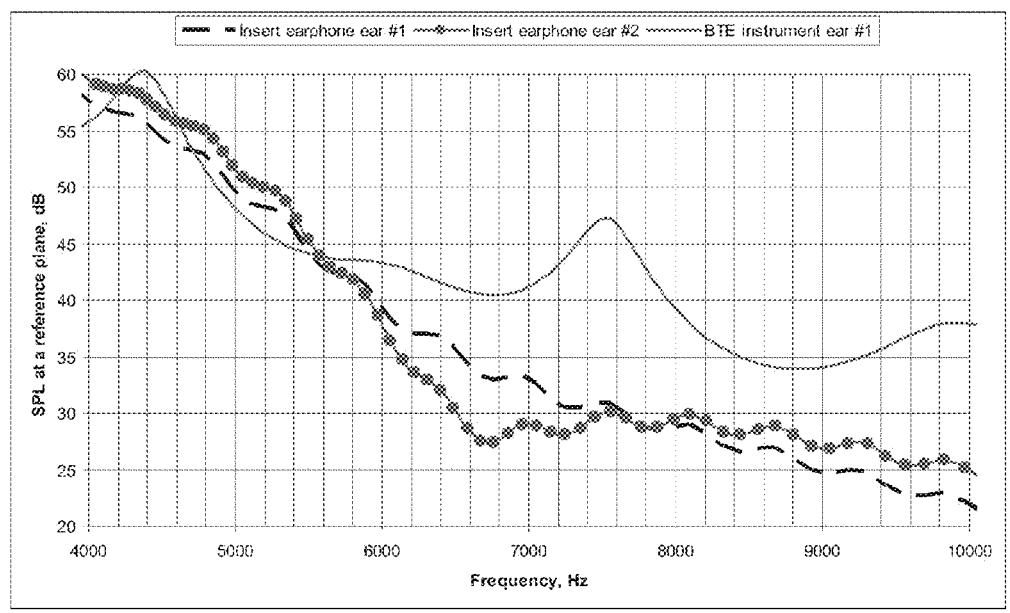
FIG. 3 is the frequency response of SPL in the ear canals measured far from the eardrum for two different sound sources and two different ears.
Figure 4:
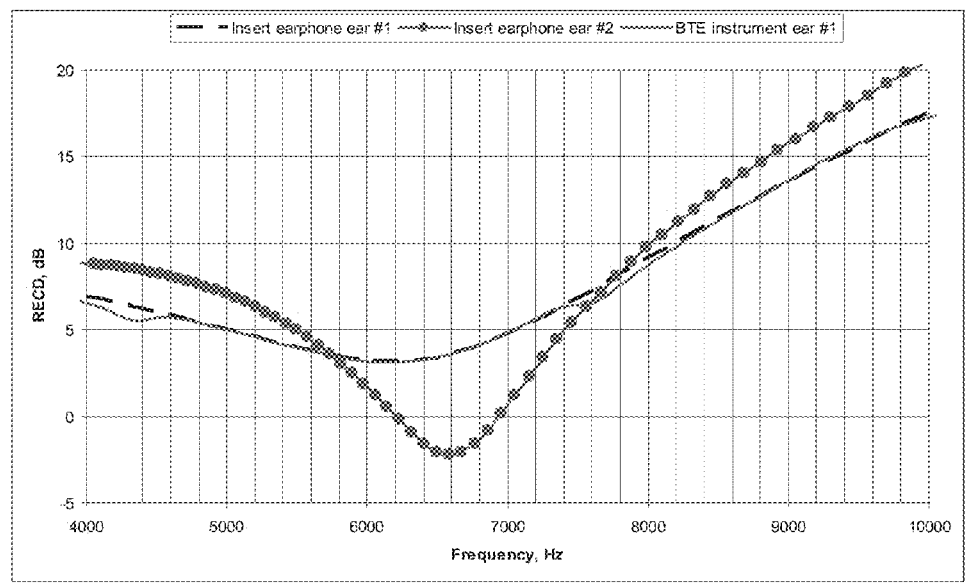
FIG. 4 is a graph of RECD curves for two different sound sources and two different ears as in FIG. 3.
Figure 5:
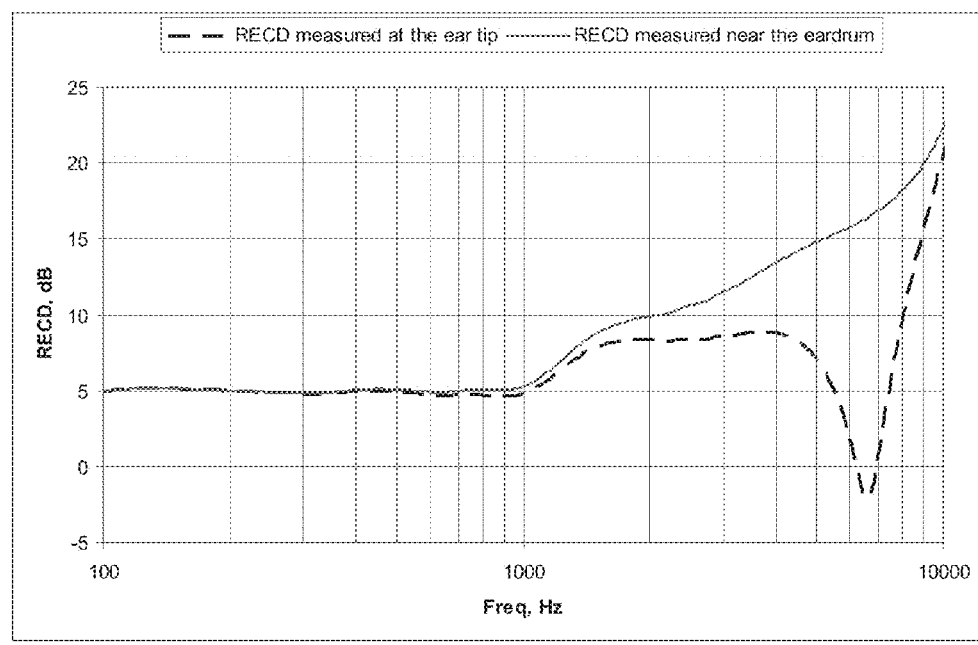
FIG. 5 is a graph of RECD measured by a probe microphone that was positioned near the eardrum and near the sound source.

The present invention provides an improved method of measuring RECD. In particular, the present invention provides a method of identifying and using the effect of the ear canal resonance by using RECD response. Since an RECD response is obtained as a difference of the results of two measurements made for the same sound source on two different loads (i.e., the occluded ear canal and, for example, a 2 cc volume of an HA-1 coupler), many irregularities of an individual frequency response get eliminated and the resulting RECD curve will mostly depend on the ratio of the impedances of the occluded ear and the 2-cc volume of the HA1 coupler. FIG. 4 illustrates the influence of the ear canal resonance on RECD showing that the ear canal resonance notch on an RECD curve can be easily identified. FIG. 5 shows a typical shape of RECD measured near the eardrum (solid line) and near the sound source, e.g., the eartip of an insert earphone (dashed line) for the ear canal length of 11 mm. The occluded canal length is 11 mm (as noted above, an average ear canal of an adult).

Figure 6:
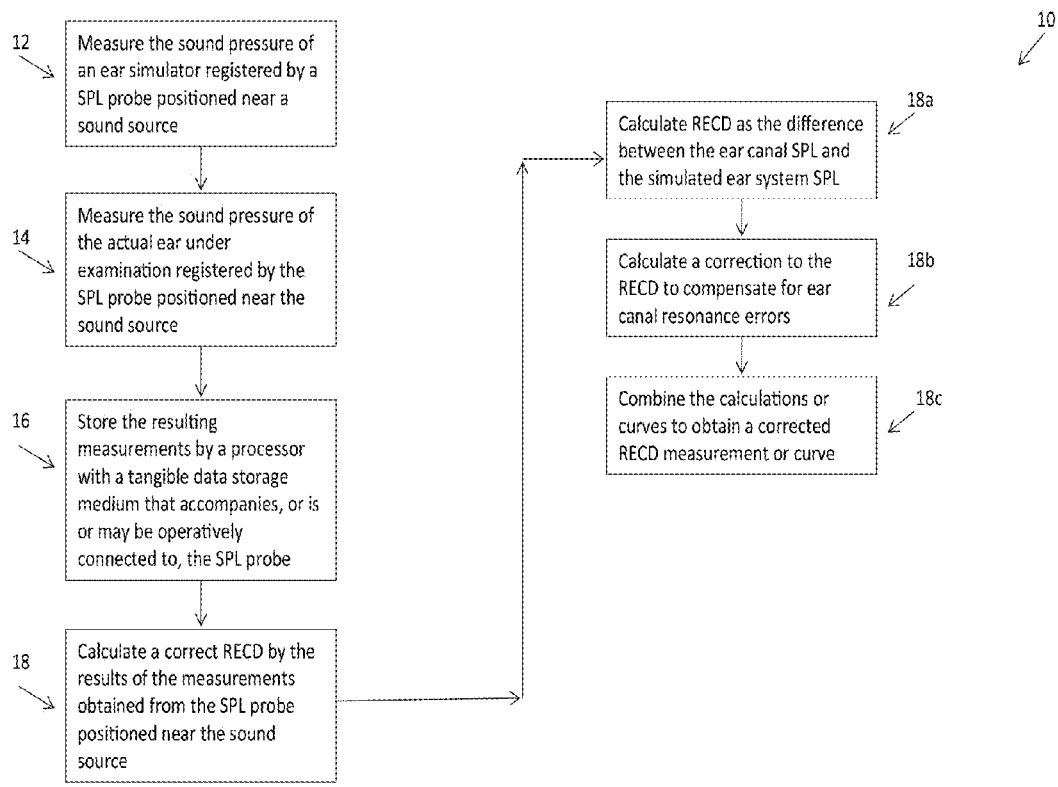
FIG. 6 is a flow chart of a method of obtaining an RECD measurement in accordance with the present invention.

FIG. 6 is a block diagram of a method 10 carried out in accordance with the present invention. The method 10 generally compensates for RECD measurement errors caused by standing waves in the occluded ear canal. The method 10 accomplishes this by characterizing the correction curve by the shape of the RECD curve near the notch caused by the ear canal resonance. The method 10 starts by measuring the sound pressure of an ear simulator registered by a SPL probe positioned near a sound source with a high impedance (Step 12). The SPL probe may be in the form of a typically-used probe microphone. The SPL probe may also be in the form of a specially-adapted microphone of a hearing aid facing the ear canal. The conventional 2 cc coupler, such as the HA-1 coupler, can be used for RECD measurements and the sound source may be, for example, an insert earphone or an appropriate hearing aid. The ear simulator may also comprise a specially-adapted coupler with an internal volume less than 2 cc. The method 10 also measures the sound pressure of the actual ear under examination registered by the SPL probe positioned near the sound source (Step 14). Both SPL measurements are made over the same frequency range of the sound generated by the sound source, for example 0.1-10 kHz. The resulting measurements are stored by a processor with a tangible data storage medium that accompanies, or is or may be operatively connected to, the SPL probe (Step 16). The measurements may then be manipulated, retrieved, and visualized using an appropriate user interface. As shown in the figures, the SPL measurements, as well as the derived RECD, are typically presented in 2D graph formats.

The method 10 then calculates a correct RECD by the results of the measurements obtained from the SPL probe positioned near the sound source (Step 18). Specifically, the method 10 calculates RECD as the difference between the ear canal SPL and the SPL in the 2 cc coupler (Step 18a) and calculates a correction to the RECD to compensate for ear canal resonance errors (Step 18b). The RECD calculation is done over the entire frequency range of the sound source and results in an RECD curve (when visualized). The RECD correction calculation is done over the same frequency range and uses a parameter of the notch (¼ wavelength ear canal resonance) in the RECD calculation (or curve). More particularly, the method 10 uses measurements of the frequency of the ear canal resonance and its specific frequencies (at −3 dB from the level at the ear canal resonance). This results in a required correction RECD curve (when visualized). The method 10 then combines the calculations or curves to obtain a corrected RECD measurement or curve (Step 18c).

Figure 7:
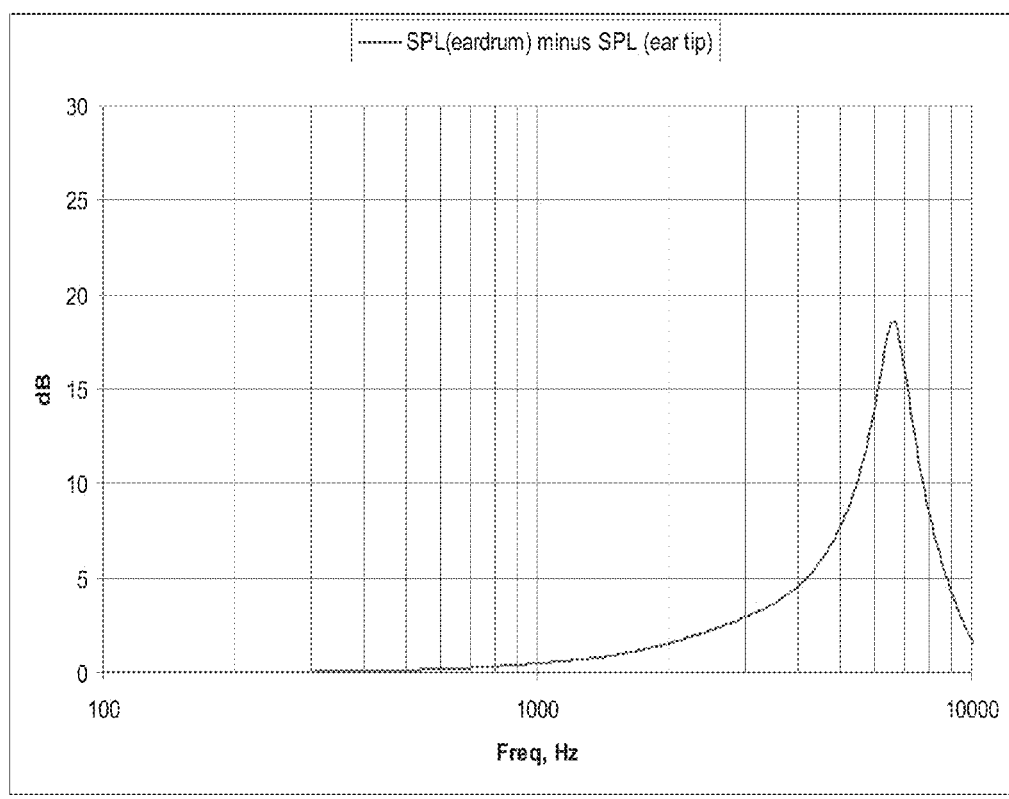
FIG. 7 is a graph of a typical shape of a correction curve for RECD measurements.

A correction curve may be calculated as a frequency response of a complex transfer function. FIG. 7 shows a typical shape of the correction curve for compensation of errors related to the ear canal resonance. The correction values expressed in dB can be calculated as follows:

$$\mathrm{Corr} = 20 * \log\left|\frac{s*K}{(s*K)^2 + \frac{s*K}{Q} + 1} + 1\right|,$$

where
$s := i \cdot 2 \cdot \pi \cdot f$, a complex operator;
$i := \sqrt{-1}$;
f is the current frequency in Hz;
Q is the quality factor of the notch;
K is a frequency scaling factor equal to $\pi/(20*F)$; and
F is the frequency of the notch in Hz.

Figure 8:
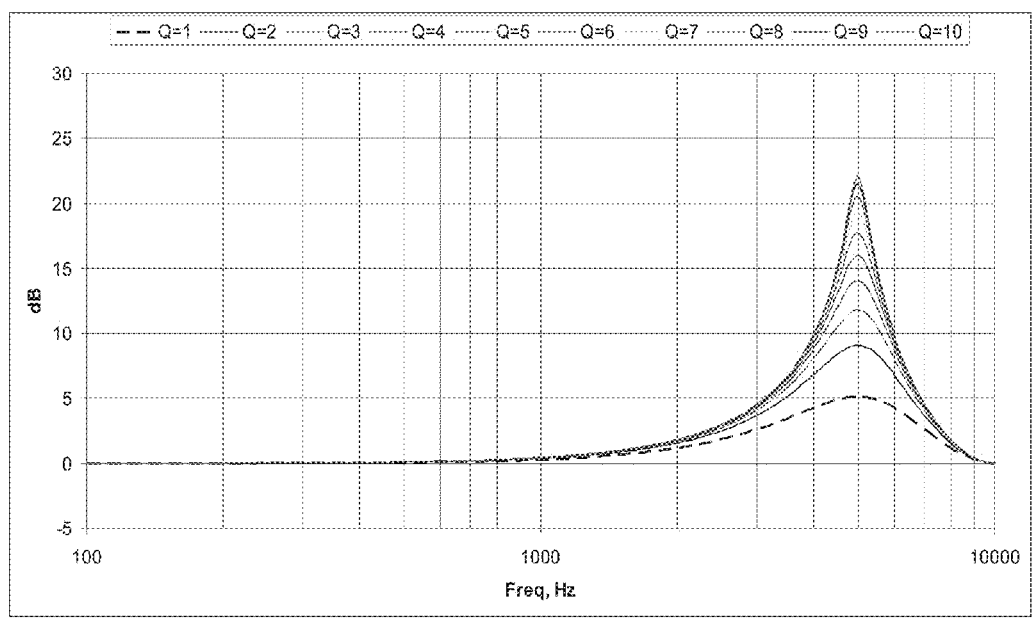
FIG. 8 is a set of calculated correction curves.

The current frequency f is the frequency at which a respective correction value Corr is to be obtained. The current frequency f may be specified to be any value in the range of 100 Hz-10 kHz. The calculation is done over the entire frequency range of the sound source. FIG. 8 shows a set of correction curves calculated, using the above equation, for the notch frequency F0 of 5 kHz and a quality factor Q varying from 1 to 10. The calculation may be performed, for example, by the processor and tangible data storage medium noted above.

Figure 9:
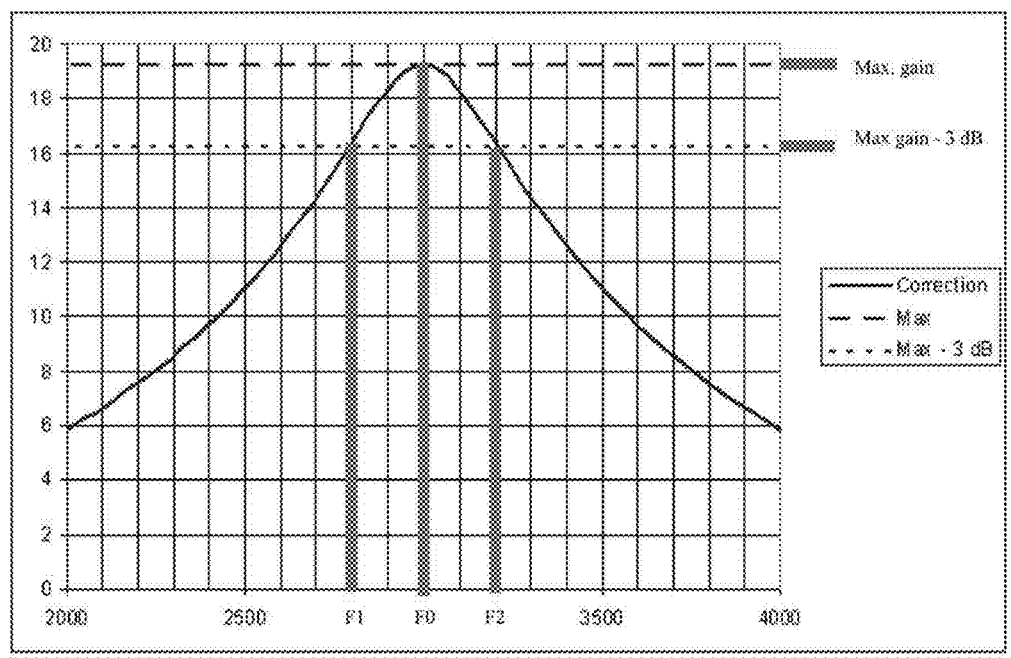
FIG. 9 illustrates the definitions of the parameters of a correction curve.
Figure 10:
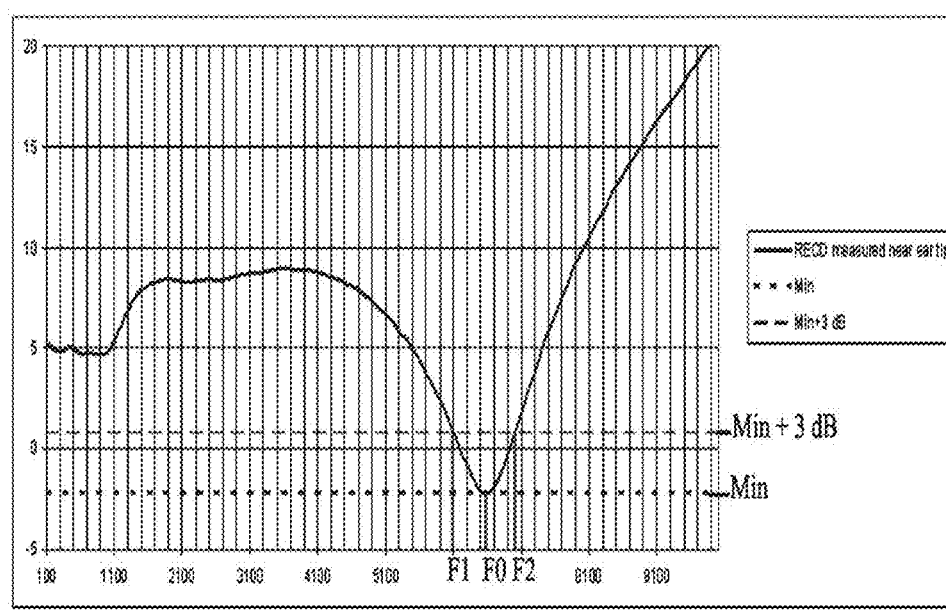
FIG. 10 illustrates the definitions of the parameters of an uncorrected RECD curve.

The method 10 is further explained by reference to FIGS. 9 and 10, which illustrate the parameters of a correction curve and an uncorrected RECD curve, respectively. FIG. 9 illustrates the definition of the parameters of a correction curve, specifically, the peak frequency F0, the maximum gain, the frequencies F1 and F2 for the gain=maximum gain minus 3 dB. The x-axis represents the sound source frequency signal measured in Hertz (Hz) and the y-axis represents the RECD correction measured in decibels (dB). FIG. 10 illustrates the definition of the parameters of the correction curve based on an uncorrected RECD curve with a notch related to the ear canal resonance, specifically, the notch frequency F0, the minimum gain, the frequencies F1 and F2 for the gain=minimum gain+3 dB. These parameters are used for calculation of the quality factor Q of the notch as Q=F0/(F2−F1). The x-axis represents the sound source frequency signal measured in Hertz (Hz) and the y-axis represents the RECD taken near the sound source measured in decibels (dB).

Figure 11:
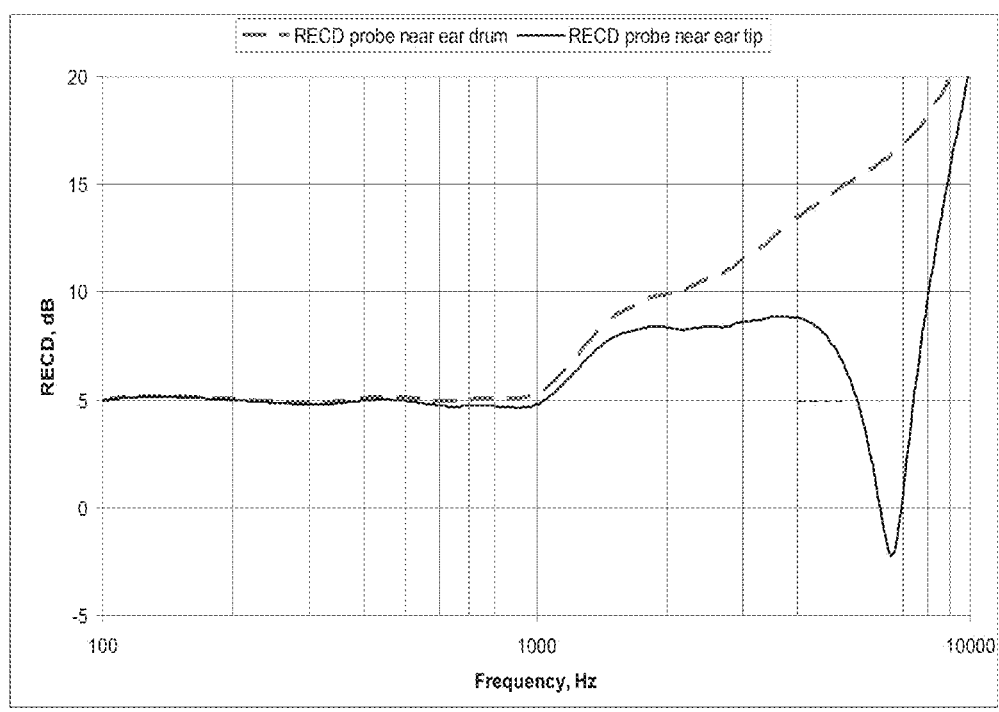
FIG. 11 is a graph of RECD measured by a probe microphone that was positioned near the eardrum and near the sound source.
Figure 12:
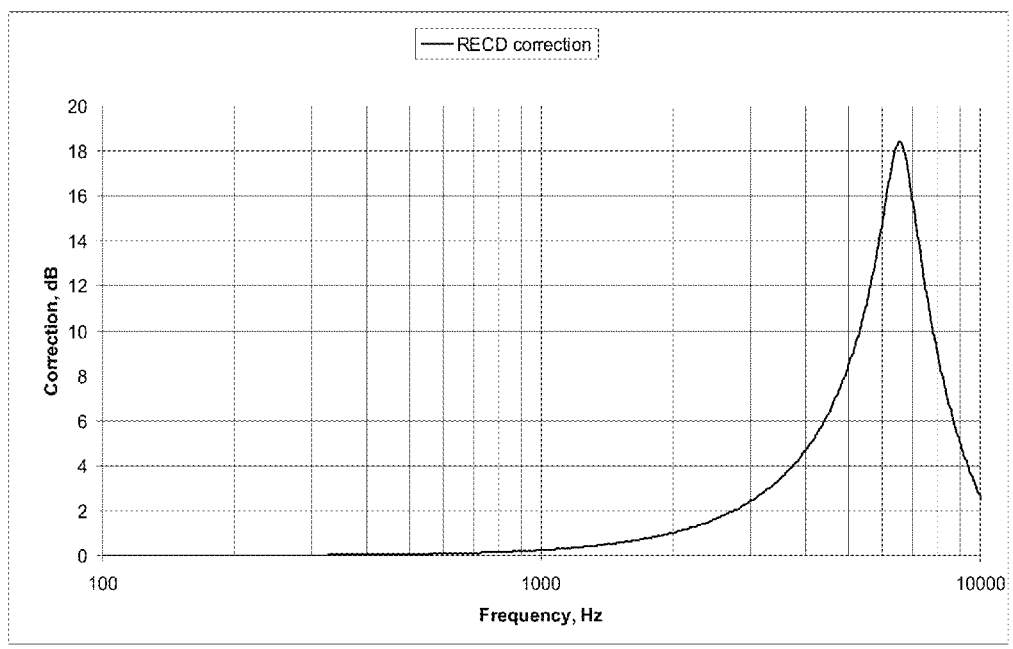
FIG. 12 is the correction curve generated for the RECD of FIG. 11.
Figure 13:
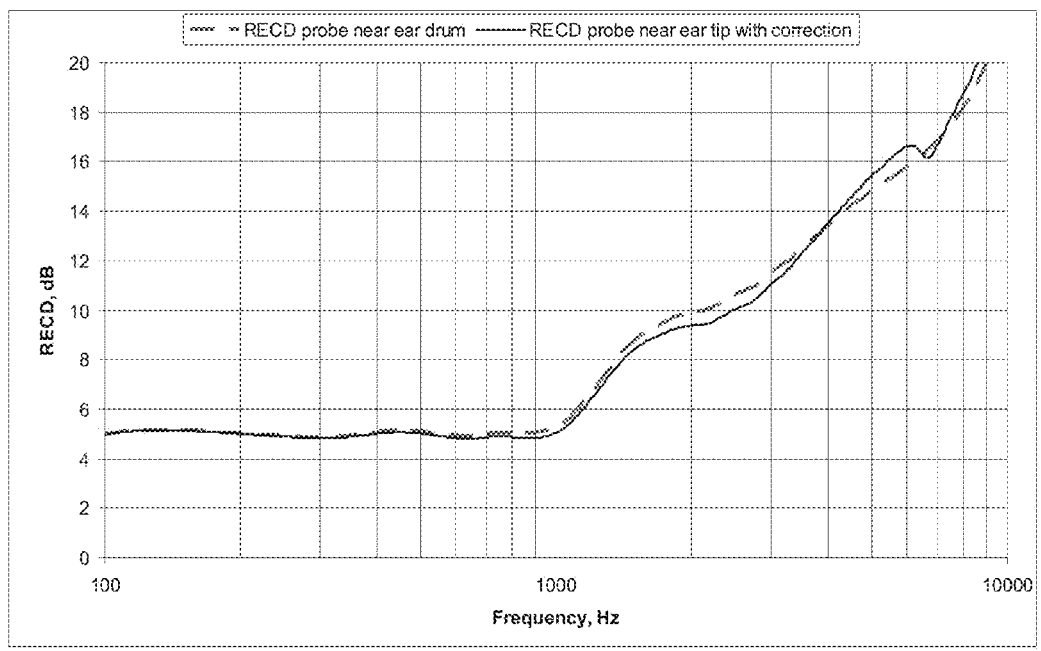
FIG. 13 is a graph of RECD measured with the probe microphone near the eardrum and near the sound source corrected for the ear canal resonance using the correction curve of FIG. 12.

Using the method 10, a corrected RECD curve was actually generated as explained with reference to FIGS. 11-13. FIG. 11 shows an example of RECD measured with a probe microphone near the eardrum (dashed line) and near the sound source e.g., the eartip of an insert earphone (solid line). The notch frequencies caused by the ear canal resonance were F0=6.69 kHz; F1=5.13 kHz; and F2=7.15 kHz and the quality factor was Q=6.43. After applying the steps of the method 10 described above, a correction curve for compensation of the RECD notch of FIG. 11 was generated. This is shown is FIG. 12. The correction curve was generated with the following parameters: F0=6.69 kHz and Q=6.43. After application of the correction curve, a corrected RECD curve measured with the probe microphone near the eardrum (dashed line) and near the sound source (solid line) were each obtained. This is shown in FIG. 13. As explained above, the RECD curve is corrected for the ear canal resonance.

Other modifications are possible within the scope of the invention. For example, the subject patient to be scanned may be a human subject, animal subject or any other suitable object. Also, the RECD calculation and the RECD correction calculation may be done over the entire frequency range of the sound source or a selected frequency range. Also, although the steps of the method 10 have been described in a specific sequence, the order of the steps may be re-ordered in part or in whole and the steps may be modified, supplemented, or omitted as appropriate. Also, the method 10 may use various well known algorithms and software applications to implement the steps and substeps. Further, the method 10 may be implemented in a variety of algorithms and software applications. Further, the method 10 may be supplemented by additional steps or techniques. It is also understood that the method 10 may carry out all or any of the steps using real-time data, stored data from a data archive or database, data from a remote computer network, or a mix of data sources.

Also, the various described instrumentation and tools are conventional and well known. They may be configured and interconnected in various ways as necessary or as desired. Further, although in the described method 10 the health professional may use self-contained instrumentation and tools, the health professional may use other instrumentation or tools in combination with or in place of the instrumentation and tools described for any step or all the steps of the method 10, including those that may be made available via telecommunication means. Further, the described method 10, or any steps, may be carried out automatically by appropriate instrumentation and tools or with some manual intervention.

What is claimed is:

1. A method of compensating for sound pressure measurement errors caused by ear canal resonance occurring in an occluded ear canal, comprising:
   a. measuring the sound pressure of a sound source in an ear simulator;
   b. measuring the sound pressure of the sound source in the ear canal;
   c. carrying out both sound pressure measurements over a frequency range of the sound source;
   d. calculating over the measured frequency range a real-ear-to-coupler difference (RECD) measurement using the sound pressure measurements;
   e. identifying a frequency notch in the calculated RECD measurement associated with ear canal resonance; and
   f. calculating a corrected RECD measurement including calculating a correction to the RECD measurement using the identified frequency notch to compensate for errors caused by ear canal resonance and combining the RECD measurement calculation and the correction calculation to obtain the corrected RECD measurement.

2. The method of claim 1, wherein calculating a corrected RECD measurement comprises measuring the frequency of the ear canal resonance and its specific frequencies at −3 dB from the level at the ear canal resonance.

3. The method of claim 1, wherein the measuring the sound pressure of the sound source in the ear canal comprises measuring the sound pressure of the sound source in the ear canal near a reference plane of the ear.

4. The method of claim 1, wherein the sound pressure is registered by a sound pressure level (SPL) probe positioned near the sound source.

5. The method of claim 3, wherein the sound pressure measurements are stored by a processor with a tangible data storage medium that may be operatively connected to the SPL probe.

6. The method of claim 3, wherein the SPL probe comprises a probe microphone.

7. The method of claim 3, wherein the SPL probe comprises a specially-adapted microphone of a hearing aid facing the ear canal.

8. The method of claim 1, wherein the ear simulator comprises a 2 cc coupler.

9. The method of claim 1, wherein the ear simulator comprises a specially-adapted coupler with an internal volume less than 2 cc.

10. The method of claim 1, wherein the sound source comprises an insert earphone or a hearing aid.

11. The method of claim 2, wherein calculating a corrected RECD measurement comprises calculating the correction as a frequency response of a complex transfer function over a selected frequency range.

12. The method of claim 11, wherein parameters of the complex transfer function comprise the identified frequency notch and the quality factor of the frequency notch.

13. The method of claim 1, wherein the step of calculating a corrected RECD measurement comprises calculating the correction using the following:

$$\text{Corr} = 20 * \log\left|\frac{s*K}{(s*K)^2 + \frac{s*K}{Q} + 1} + 1\right|,$$

where $s := i2\pi f$, a complex operator; $i := \sqrt{-1}$; f is the current frequency in Hz; Q is the quality factor of the notch; K is a frequency scaling factor equal to $\pi/(20*F)$; and F is the frequency of the notch in Hz.

14. The method of claim 13, wherein the current frequency f comprises a value in the range of 100 Hz-10 kHz.

* * * * *